United States Patent [19]
Killion et al.

[11] Patent Number: 5,921,957
[45] Date of Patent: *Jul. 13, 1999

[54] INTRAVASCULAR DILATION CATHETER

[75] Inventors: Douglas P. Killion; David W. Lodin, both of Maple Grove, Minn.

[73] Assignee: SCIMED Life Systems, Inc., Maple Grove, Minn.

[*] Notice: This patent is subject to a terminal disclaimer.

[21] Appl. No.: 08/274,071

[22] Filed: Jul. 12, 1994

[51] Int. Cl.$^6$ .................................................. A61M 29/00
[52] U.S. Cl. .............................. 604/96; 606/192; 606/194
[58] Field of Search .................................. 604/96, 97, 98, 604/99, 101, 102, 103, 104, 264, 280

[56] References Cited

U.S. PATENT DOCUMENTS

| | | |
|---|---|---|
| 2,667,875 | 2/1954 | Wallace . |
| 3,828,767 | 8/1974 | Spiroff . |
| 4,114,625 | 9/1978 | Onat . |
| 4,214,593 | 7/1980 | Imbruce et al. . |
| 4,323,071 | 4/1982 | Simpson et al. . |
| 4,361,152 | 11/1982 | Patel . |
| 4,464,176 | 8/1984 | Wijayarathna . |
| 4,571,240 | 2/1986 | Samson et al. . |
| 4,588,398 | 5/1986 | Daugherty et al. . |
| 4,597,755 | 7/1986 | Samson et al. . |
| 4,606,347 | 8/1986 | Fogarty et al. . |
| 4,638,805 | 1/1987 | Powell . |
| 4,641,654 | 2/1987 | Samson et al. . |
| 4,670,009 | 6/1987 | Bullock . |
| 4,684,323 | 8/1987 | Field . |
| 4,723,556 | 2/1988 | Sussman . |
| 4,752,286 | 6/1988 | Okada . |
| 4,775,371 | 10/1988 | Mueller, Jr. . |
| 4,782,834 | 11/1988 | Maguire et al. . |
| 4,793,351 | 12/1988 | Landman et al. . |
| 4,813,934 | 3/1989 | Engelson et al. . |
| 4,848,344 | 7/1989 | Sos et al. . |
| 4,850,969 | 7/1989 | Jackson . |
| 4,892,519 | 1/1990 | Songer et al. ............................. 604/96 |
| 4,909,258 | 3/1990 | Kunt et al. . |
| 4,917,666 | 4/1990 | Solar et al. . |
| 4,921,483 | 5/1990 | Wijoy et al. . |
| 4,927,418 | 5/1990 | Dake et al. . |
| 4,932,959 | 6/1990 | Horzewski et al. . |
| 4,955,895 | 9/1990 | Sugiyama et al. . |
| 4,964,853 | 10/1990 | Sugiyama et al. . |
| 4,995,865 | 2/1991 | Gahara et al. . |
| 5,015,232 | 5/1991 | Maglinte . |
| 5,021,044 | 6/1991 | Sharkawy . |
| 5,021,045 | 6/1991 | Buckberg et al. . |
| 5,035,694 | 7/1991 | Kasprzyk et al. . |
| 5,041,083 | 8/1991 | Tsuchida et al. . |

(List continued on next page.)

OTHER PUBLICATIONS

"Balloon Catheters and Systems for Transluminal Angioplasty," Medi–tech, Inc., 16 pgs.

*Primary Examiner*—Corrine M. McDermott
*Assistant Examiner*—N Kent Gring
*Attorney, Agent, or Firm*—Robert E. Atkinson

[57] ABSTRACT

A balloon dilation catheter which has a long shaft and an inflatable balloon connected to its distal end. The shaft includes a guide wire lumen which has an inner diameter that is substantially larger than the guide wire diameter used in the procedure. An atraumatic tip is connected to the distal end of the inflatable balloon and includes an aperture which the guide wire passes through. The diameter of the aperture remains constant but is substantially less than the inner diameter of the guide wire lumen and matches the maximum diameter of the guide wire used in the procedure. The atraumatic tip minimizes the potential for vascular damage and eliminates the need to change catheters or guide wires and thus reduces the time and cost of the PTA procedure. The tip also includes holes which allow for dye injection and pressure measurement while the guide wire extends through the aperture. Alternatively, the aperture may be compliant such that it can expand or contract to accommodate guide wires of different diameters. The compliant tip minimizes the circumferencial ledge between the distal end of the catheter and the guide wire and thereby minimizes the potential for vascular damage.

18 Claims, 4 Drawing Sheets

U.S. PATENT DOCUMENTS

| | | |
|---|---|---|
| 5,053,004 | 10/1991 | Markel et al. . |
| 5,059,176 | 10/1991 | Winters . |
| 5,078,681 | 1/1992 | Kawashima . |
| 5,085,635 | 2/1992 | Cragg . |
| 5,085,636 | 2/1992 | Burns . |
| 5,114,423 | 5/1992 | Kasprzyk et al. . |
| 5,135,494 | 8/1992 | Engelson et al. . |
| 5,135,599 | 8/1992 | Martin et al. . |
| 5,141,518 | 8/1992 | Hess et al. . |
| 5,147,385 | 9/1992 | Beck et al. . |
| 5,171,221 | 12/1992 | Samson . |
| 5,176,661 | 1/1993 | Evard et al. . |
| 5,188,593 | 2/1993 | Martin . |
| 5,195,971 | 3/1993 | Sirhan ................................ 604/96 |
| 5,197,948 | 3/1993 | Ghodsian . |
| 5,197,951 | 3/1993 | Mahurkar . |
| 5,209,729 | 5/1993 | Hofmann et al. . |
| 5,221,256 | 6/1993 | Mahurkar . |
| 5,242,395 | 9/1993 | Maglinte . |
| 5,242,396 | 9/1993 | Evard . |
| 5,250,034 | 10/1993 | Appling et al. . |
| 5,250,069 | 10/1993 | Nobuyoshi et al. . |
| 5,295,961 | 3/1994 | Niederhauser et al. . |
| 5,308,323 | 5/1994 | Sogawa et al. . |
| B1 4,323,071 | 4/1982 | Simpson et al. . |

# INTRAVASCULAR DILATION CATHETER

FIELD OF THE INVENTION

The present invention generally relates to intravascular catheters. More specifically, the present invention relates to PTA balloon catheters. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well known in the art and typically involve the use of a balloon catheter and a guide wire, possibly in combination with other intravascular devices. The balloon catheter is advanced over the guide wire such that the distal end of the balloon catheter is positioned adjacent a restriction in a diseased vessel. The balloon is inflated and the restriction in the vessel is opened, thus restoring normal blood flow.

While many PTCA and PTA devices are well known in the art, PTA has several unique technical and clinical challenges which prior art devices do not overcome. For example, typical PTA guide wire diameters range from about 0.018 inches to about 0.035 inches. The size of the guide wire used may depend on the preference of the physician, the desired vascular site, the morphology of the vasculature, the pressure monitoring capabilities necessary, the dye injection capabilities necessary and/or other device(s) to be used in conjunction with the guide wire. A physician may select or exchange several guide wire and catheter combinations to accommodate the diagnostic and therapeutic requirements of the procedure.

It is generally desirable to have a catheter which is matched to the specific size of the guide wire in use. The word matched in this instance means that the diameter of the distal end of the guide wire is about the same or just slightly less than the diameter of the distal end of the guide wire lumen. Matching the guide wire size to the catheter size avoids scraping, coring or carving vascular tissue when crossing a lesion or entering a puncture site without an introducer sheath. Scraping occurs when a catheter is used with an under-sized guide wire such that a circumferencial ledge is created between the guide wire and the distal of the catheter. The circumferencial ledge tends to scrape, core and carve vascular tissue creating unnecessary damage and increased potential for complications. To avoid these risks, a treating physician can match the catheter and guide wire sizes in order to minimize the circumferencial ledge. However, matching the catheter size to the size of the guide wire compromises the ability of the physician to take pressure measurements or inject contrast dye through the guide wire lumen with the guide wire in place. In addition, changing catheters or guide wires during the procedure increases the time and cost of the procedure. Thus, while a matched guide wire and catheter combination avoids the scraping problem, it increases the required time for a procedure, increases the cost of the procedure, compromises the ability of the physician to take pressure measurements and compromises the ability of the physician to inject contrast dye.

In view of the disadvantages of prior art catheters, it is desirable to have a single catheter which matches the size of a guide wire while maintaining the ability to measure pressure gradients and inject contrast dye with the guide wire in place. Such a catheter would minimize or eliminate the circumferencial ledge and thus minimize the resulting potential for vascular damage. In addition, such a catheter would eliminate the need to change catheters or guide wires and thus reduce the time and cost of the PTA procedure.

SUMMARY OF THE INVENTION

The present invention satisfies these desires and overcomes the disadvantages of the prior art in a novel and non-obvious manner. One embodiment of the present invention is a balloon dilation catheter which has a long shaft with an inflatable balloon connected to its distal end. The shaft includes a guide wire lumen which has an inner diameter that is substantially larger than the maximum guide wire diameter used in the procedure. An atraumatic tip is connected to the distal end of the inflatable balloon and includes an aperture which the guide wire passes through. The diameter of the aperture remains constant but is substantially less than the inner diameter of the guide wire lumen and matches the maximum diameter of the guide wire used in the procedure. The atraumatic tip minimizes the potential for vascular damage and eliminates the need to change catheters or guide wires and thus reduces the time and cost of the PTA procedure. The tip also includes holes which allow for dye injection and pressure measurement while the guide wire extends through the aperture.

Another embodiment of the present invention is a balloon dilation catheter which has a long shaft with an inflatable balloon connected to its distal end. A flexible tip is connected to the distal end of the inflatable balloon and includes an aperture which the guide wire passes through. The aperture is compliant such that it can expand or contract to accommodate guide wires of different diameters. The compliant tip minimizes the circumferencial ledge and thereby minimizes the potential for vascular damage. In addition, the compliant tip eliminates the need to change catheters or guide wires and thus reduces the time and cost of the PTA procedure. The tip may also include holes which allow for dye injection and pressure measurement while the guide wire extends through the aperture.

In practice, the first embodiment of the present invention may be used in the following manner. A guide wire is inserted into the vascular system. A balloon catheter is slid over the guide wire either before or after the guide wire is inserted into the vasculature. The catheter includes a guide wire lumen extending therethrough and an aperture located at the distal end of the guide wire lumen. The diameter of the guide wire is substantially less than the inside diameter of the guide wire lumen and is substantially the same as the diameter of the aperture. Dye injections or pressure measurements may be taken through the guide wire lumen with the guide wire in place.

While the disclosure focuses on balloon dilation catheters and methods of use thereof, those skilled in the art will recognize that the invention may be incorporated into other devices and methods of use not discussed herein. Furthermore, in addition to the advantages described, other advantages of the present invention can be appreciated without departing from the spirit of the invention.

DETAILED DESCRIPTION OF THE INVENTION

The following detailed description should be read with reference to the drawings in which like elements in different figures are numbered identically. The materials, dimensions and methods of manufacture are conventional and known in the art unless otherwise specified.

Figure 1:
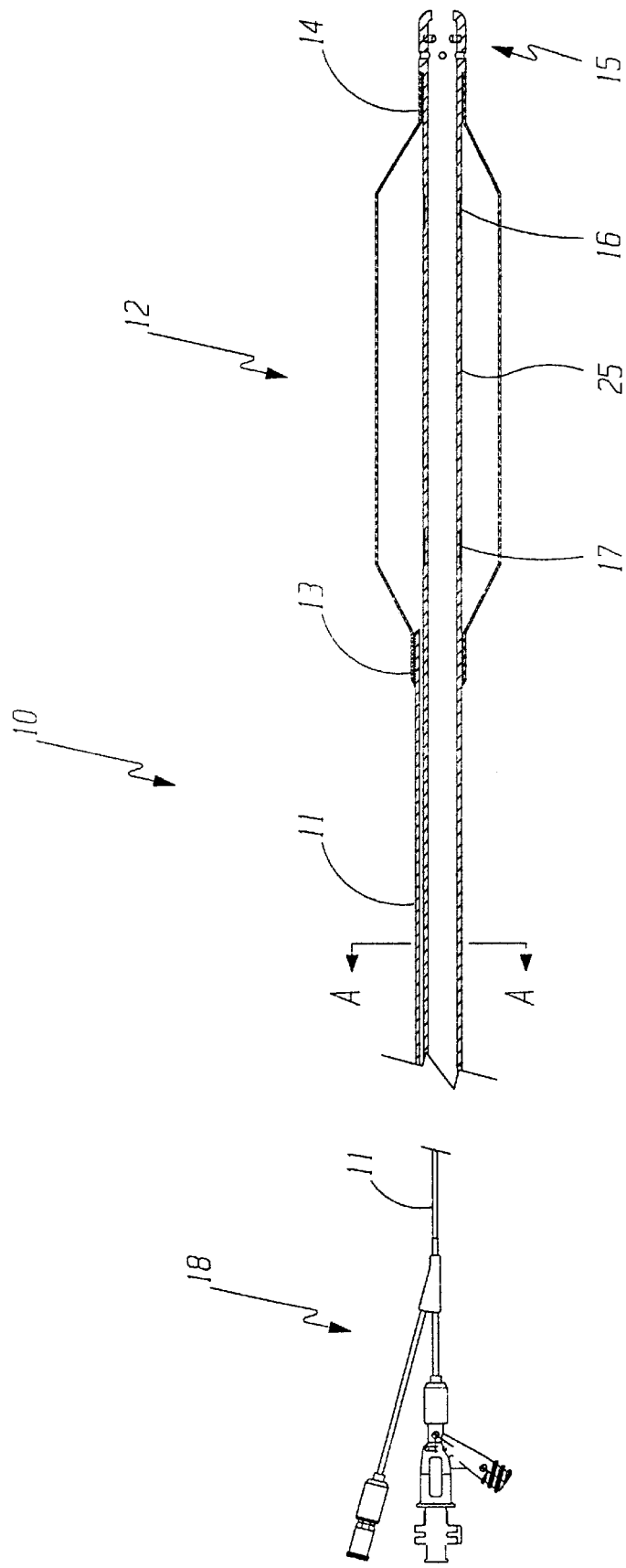
FIG. 1 is a partially sectioned side view of a preferred embodiment of the present invention.

Referring to FIG. 1, a partially sectioned side view of a preferred embodiment of the balloon catheter 10 is shown. The balloon catheter 10 includes an elongate shaft 11 with an inflatable balloon 12 connected at its distal end. The balloon 12 includes a proximal waist 13 connected to the shaft 11 and a distal waist 14 connected to the formed guide wire tube 25. A tip 15 is connected to the distal balloon waist 14 and the distal end of the formed guide wire tube 25. Radiopaque marker bands 16, 17 are secured to the formed guide wire tube 25 and are positioned to designated the working length of the balloon 12. A manifold 18 is secured to the proximal end of the shaft 11 to facilitate fluid connection to an inflation device and a flush syringe.

Figure 2:
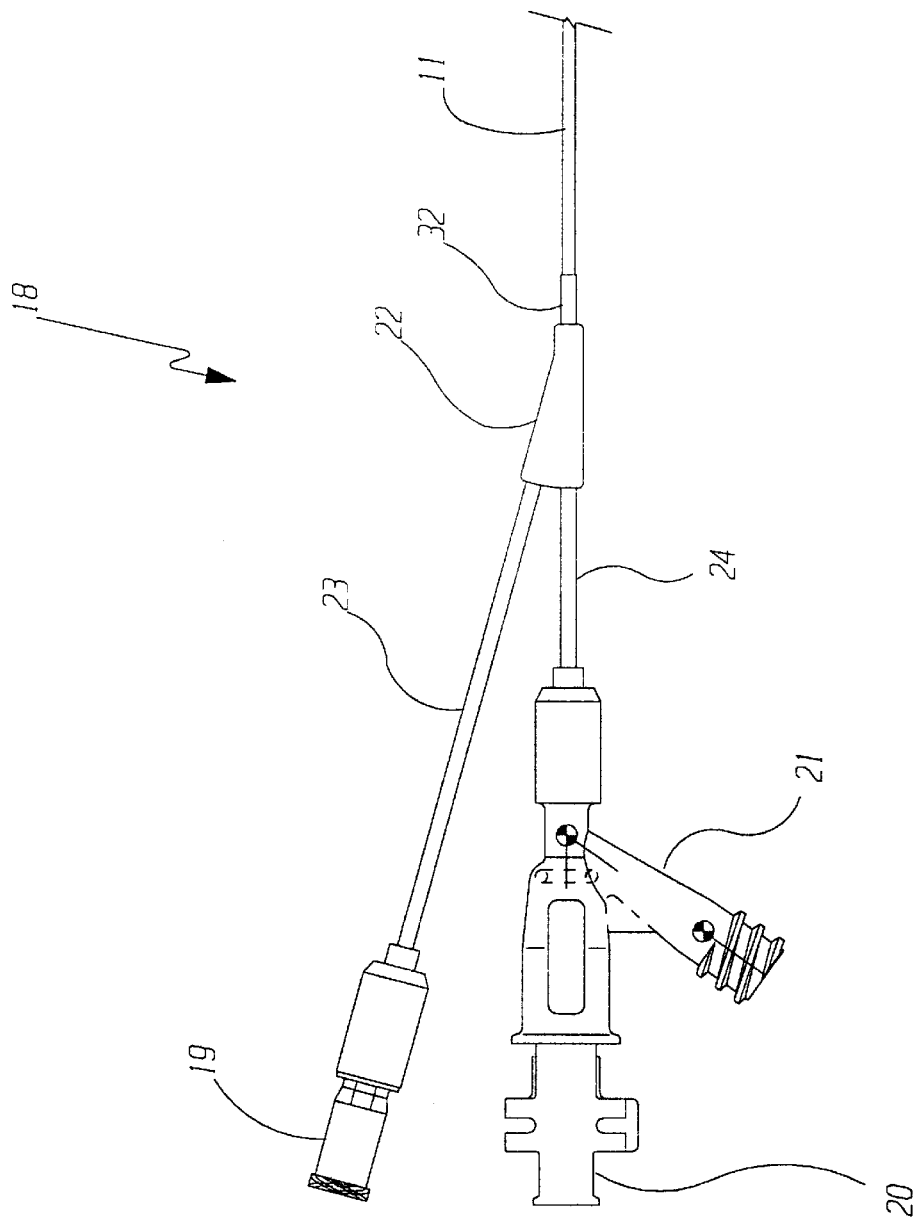
FIG. 2 is a side view of a proximal end of a preferred embodiment of the present invention.
Figure 3:
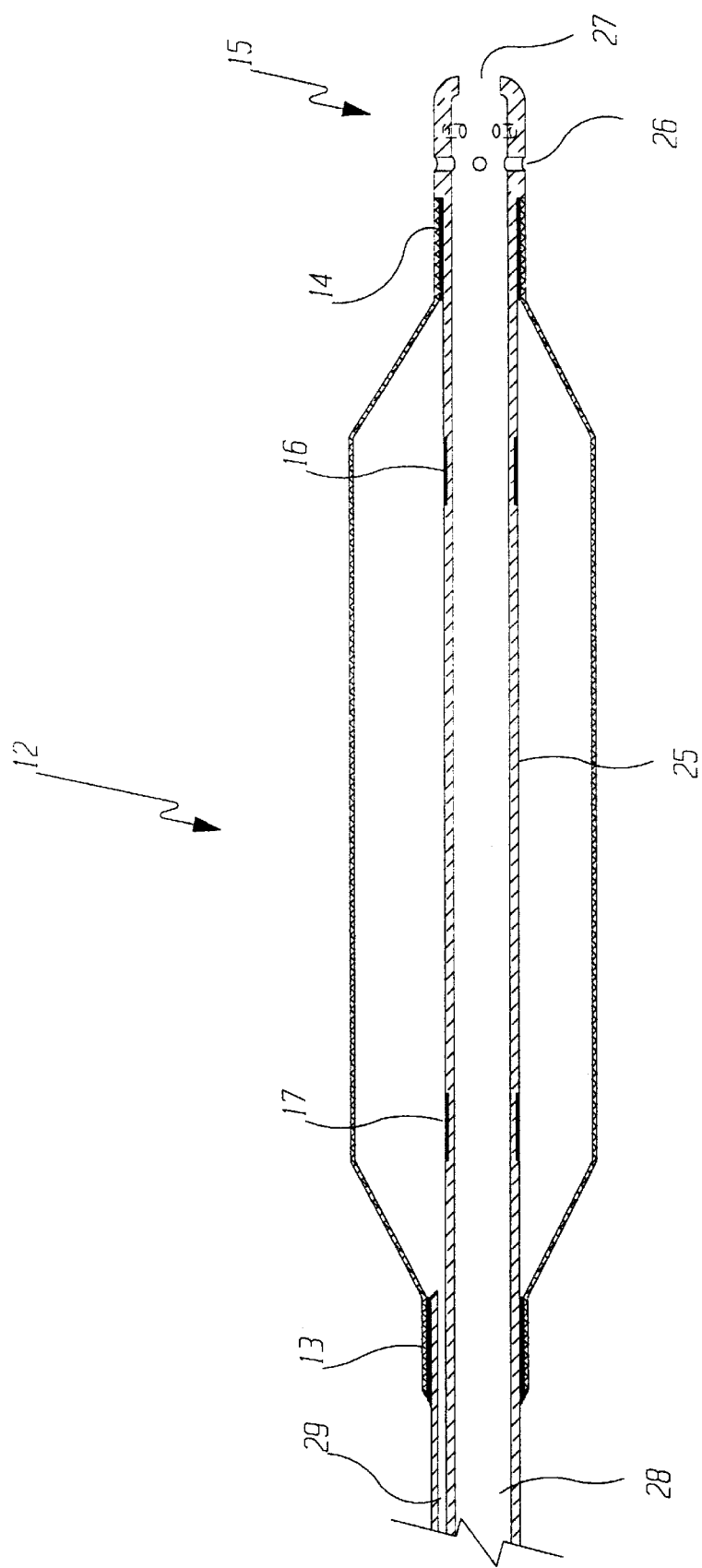
FIG. 3 is a longitudinally sectioned side view of a distal end of a preferred embodiment of the present invention.
Figure 4:
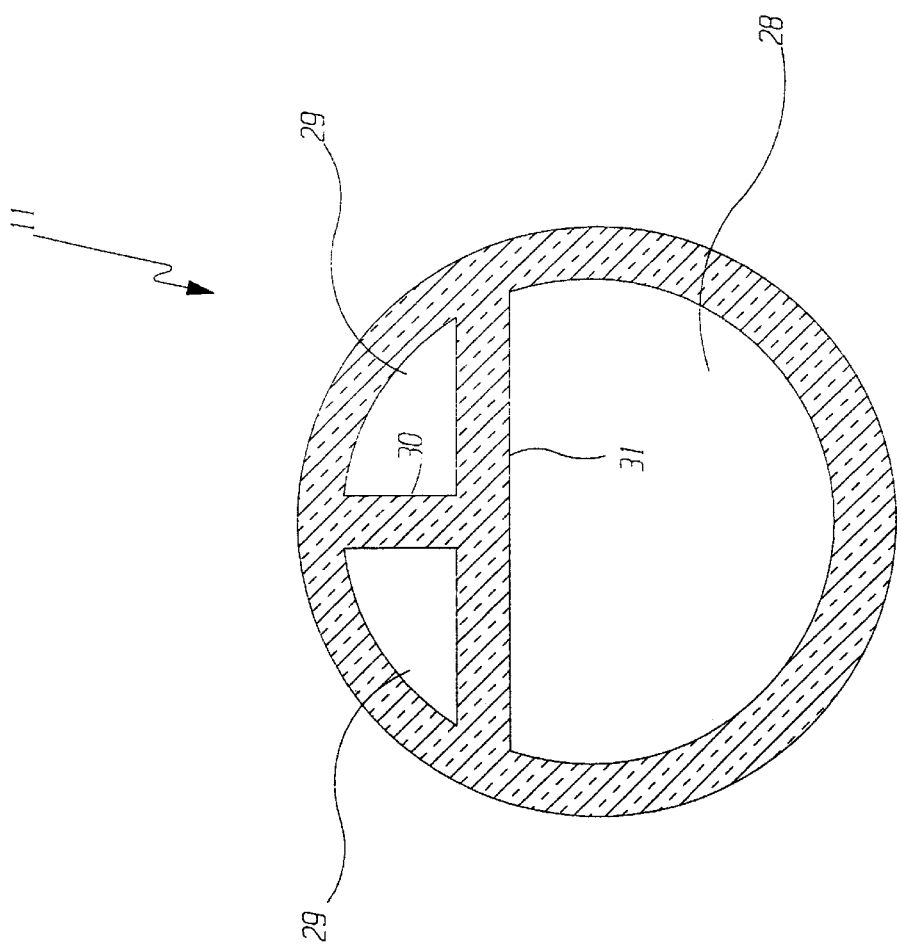
FIG. 4 is a cross sectional view taken at A—A in FIG. 1.

Referring now to FIG. 2, a side view of the preferred embodiment of the manifold 18 is shown. Those skilled in the art will recognize that there are several conventional manifold designs usable with the present invention. The preferred manifold 18 is connected to the proximal end of the shaft 11 at hub 22. A strain relief 32 is placed about the transition from the relatively stiff hub 22 to the relatively flexible shaft 11 and serves to reduce the tendency of the shaft 11 to kink in that area. Hub 22 serves to separate the inflation lumen 29 and the guide wire lumen 28 (as shown in FIGS. 3 and 4) of the shaft 11 into two distinct tubes; the inflation extension tube 23 and the guide wire extension tube 24. An inflation port 19 is connected to the proximal end of the inflation extension tube 23 and includes a standard luer adapter for connection to an inflation device (not shown) which are conventional in the art. A guide wire port 20 is connected to the proximal end of the guide wire extension tube 24 and includes a standard compression o-ring seal to seal about a guide wire. A thru port 21 is also connected to the proximal end of the guide wire extension tube 24 and includes a standard luer adapter for connection to a conventional syringe or pressure gauge. The thru port 21 facilitates the injection of contrast dye, the measurement of intravascular pressure, and the flushing of the guide wire lumen 28. The combination of the guide wire port 20 and the thru port 21 is commonly referred to as a Y-adapter. The built-in Y-adapter reduces the number of ancillary devices necessary and simplifies the procedure in contrast to prior art Y-adapters which are separate from the catheter 10.

Continuing to refer to FIG. 2, the strain relief 32, the inflation extension tube 23 and the guide wire extension tube 24 are preferably made of an extruded polyamide/polyether polyester, but those skilled in the art will recognize that other suitable materials and manufacturing processes may be used. The inflation port 19, the guide wire port 20 and the thru port 21 are formed of injection molded polycarbonate, but other suitable materials and forming processes may be utilized. The guide wire extension tube 24, the inflation extension tube 23, the strain relief 32 and the shaft 11 are connected together at the hub 32 by an insert molding process. Removable mandrels are used to maintain the inflation lumen 29 and the guide wire lumen 28 (shown in FIGS. 3 and 4) during the insert molding process. The hub is preferably made of injection molded polyamide/polyether polyester but other suitable materials may be employed.

Referring now to FIG. 3, a longitudinally sectioned side view of a distal end of the preferred embodiment of the catheter 10 is shown. The balloon 12 is connected to the shaft 11 at the proximal waist 13 by a suitable adhesive such as a urethane adhesive available from H. B. Fuller. Similarly, the distal balloon waist 14 is bonded to the formed guide wire tube 25 by a suitable adhesive such as a urethane adhesive, but those skilled in the art will recognize that other medical grade adhesives, such as ultraviolet light (UV) curable adhesives may be used, as well as thermal bonds, ultrasonic bonds, etc. The balloon is preferably made of extruded and blow molded polyethylene terephthalate, but those skilled in the art will recognize that the balloon can also be made of other materials such as polyethylene, polyolefin copolymer and nylon by conventional blow molding processes.

Continuing to refer to FIG. 3, the marker bands 16, 17 are preferably made of a radiopaque material such as gold, platinum or a platinum alloy (e.g. 90% platinum, 10% iridium). To maintain the correct position on the formed guide wire tube 25, the marker bands 16, 17 are preferably separated by spacer bands, but other securing techniques such as adhesive encapsulating and heat shrink tubing may be employed. In the preferred method, a proximal spacer band is positioned between the proximal marker band 17 and the edge of the skive adjacent the proximal balloon waist 13. A middle spacer band separates the distal marker band 16 from the proximal marker band 17. A distal spacer band separates the distal marker band 16 from the bond between the distal balloon waist 14 and the formed guide wire tube 25. The spacer bands are preferably made of a polymer. Once in place, the polymer spacers are thermally re-flowed to form a smooth surface and to melt the polymer components together. The smooth surface about the formed guide wire tube 25 reduces the potential for the edges of the marker bands 16, 17 to damage the balloon 12.

With continued reference to FIG. 3, the tip 15 is preferably formed integrally with the formed guide wire tube 25 by thermally molding a distal portion of the formed guide wire tube 25 into a cup shape to define a reduced diameter aperture 27. Alternatively, the tip 15 may be formed integrally with the distal waist 14 of the balloon 12. The tip 15 can also be a separate component attached to the distal balloon waist 14 or the distal end of the formed guide wire tube 25 by means of a suitable adhesive or thermal bonding process. Holes 26 are then made by either a drilling or punching process. The holes 26 allow for pressure measurements and dye injections through the guide wire lumen 28 when the guide wire extends through the aperture 27. Two rows of four holes, each hole spaced 90 degrees apart, each hole having a diameter of about 0.017 inches, the rows spaced about 1 millimeter apart, and the rows offset by 45 degrees is preferred.

In a first embodiment wherein the catheter 10 is intended for primary use in combination with a guide wire with a diameter of about 0.035 inches, the aperture 27 remains at about 0.037 inches but is less than the inside diameter of the guide wire lumen 28, preferably about 0.051 inches. The tip 15 is preferably made of a polyamide/polyether polyester and high density polyethylene blend, but any suitable polymer may be utilized. The aperture dimensions and material may be altered to effect various performance criteria such as guide wire movement, flow characteristics, etc. Lubricious coating may also be used to improve performance criteria.

In a second embodiment wherein the catheter 10 is intended for primary use in combination with a guide wire with a diameter of about 0.018 inches, the aperture 27 is preferably about 0.018 inches in its relaxed state and can expand to about 0.037 inches to accommodate larger guide wires. The tip 15 is preferably made of a low durometer polyamide/polyether polyester, but any flexible polymer with compliant characteristics may be utilized.

In another embodiment (not shown), the tip utilizes a plurality of longitudinal slits to allow expansion and contraction of the aperture. The tip is preferably cone-shaped rather than cup-shaped for this embodiment. With the aperture in the relaxed (contracted) state, the slits are essentially closed. When the aperture expands to accommodate a larger guide wire, the slits open. Alternatively, the tip can utilize a plurality of longitudinal recesses or folds rather than slits. The folds or recesses would function similarly to slits described above. As in the preferred embodiment, holes are formed in the side of the cone-shaped tip to allow for dye injections and pressure measurements when the guide wire extends through the aperture.

Referring now to FIG. 4, a cross sectional view of the shaft 11 is shown (taken at A—A in FIG. 1). The shaft is preferably made of an extruded polyamide/polyether polyester and high density polyethylene blend, but other conventional materials may be used. A horizontal membrane 31 separates the shaft 11 into separate guide wire lumen 28 and inflation lumens 29. The vertical membrane 30 serves to prevent the horizontal membrane 31 from collapsing when under pressure. The vertical membrane may also serve to isolate an additional lumen which may be used to inject fluids, measure pressures, etc. In the preferred embodiment, the guide wire lumen 28 is sized to allow for pressure measurement and dye injections with a guide wire in place. The inflation lumens 29 are sized to allow for rapid inflation and deflation of the balloon. In a first embodiment, the extruded shaft 11 of the catheter 12 may have an outside diameter of about 0.079 inches, an inside diameter of about 0.065 inches, and a horizontal membrane 31 spaced 0.013 inches off center. Those skilled in the art will recognize that other dimensions may be used to suit the clinical application of the device.

In an alternative embodiment (not shown), the catheter shaft 11 may include two coaxial tubes in place of a single extrusion. In this embodiment, the outer tube would be connected to the proximal end of the balloon and the inner tube would be connected to the distal end of the balloon. The manifold would be connected to the proximal end of the coaxial tubes in a manner conventional in the art. The tip could be formed integrally with the distal end of the inner tube as discussed earlier.

In practice the catheter may be used in the following manner. The catheter 10 incorporates an aperture with a diameter that remains constant (preferably 0.037 inches) but is substantially less than the inner diameter of the guide wire lumen (preferably 0.051 inches) and matches the maximum diameter of the guide wire (typically 0.035 inches), a guide wire is inserted into the vasculature and the balloon catheter 10 is slid over the guide wire. The catheter 10 may be slid on the guide wire before the guide wire is inserted into the vascular system (referred to as pre-loading), such that the catheter 10 and the guide wire are inserted simultaneously. While the guide wire remains inside the catheter 10, pressure measurements and dye injections may be performed by way of connection to the thru port 21 on the manifold 18. In this alternative use and specified dimensions, laboratory tests have shown that flow rates of about 2.25 cc/sec are easily achieved with a 0.035 inch diameter guide wire in place (60 psi inlet pressure, 50/50 mix of saline and Renografin 76 contrast dye, 75 cm catheter length).

In an alternative use, the catheter 10 is typically used in the following manner. First, a first guide wire is inserted into the vascular system. Second, the balloon catheter 10 with an aperture 27 at its distal end is slid over the first guide wire and the aperture 27 assumes a diameter substantially the same as the diameter of the first guide wire. The catheter 10 may be slid on the guide wire before the guide wire is inserted into the vascular system (referred to as pre-loading), such that the catheter 10 and the guide wire are inserted simultaneously. Third, the first guide wire may be removed from the balloon catheter 10. And fourth, a second guide wire with a different diameter may be inserted into the balloon catheter and the aperture 27 on the balloon catheter 10 changes to a diameter substantially the same as the diameter of the second guide wire. Pressure measurements and dye injections may be performed with a guide wire of a suitable diameter in place by way of connection to the thru port 21 on the manifold 18.

While the specification describes the preferred constructions, materials, methods of manufacture and methods of practice, those skilled in the art will appreciate the scope and spirit of the invention with reference to the appended claims.

What is claimed is:

1. A balloon dilation catheter system, comprising:
   (i) a guide wire; and
   (ii) a balloon dilation catheter removably disposed about the guide wire, the balloon catheter comprising:
      (a) an elongate shaft having a proximal end and a distal end, the elongate shaft defining a guide wire lumen and an inflation lumen extending therethrough, the guide wire lumen having an inside diameter;
      (b) an inflatable balloon connected to the distal end of the elongate shaft, the inflatable balloon having a proximal end, a distal end and an interior in fluid communication with the inflation lumen, the guide wire lumen extending through the balloon; and
      (c) a tip connected to the distal end of the inflatable balloon, the tip defining a plurality of laterally-facing holes and a distally-facing guide wire aperture, the distally-facing guide wire aperture having a diameter less than the inside diameter of the guide wire lumen, both the distally-facing guide wire aperture and the laterally-facing holes being in fluid communication with the guide wire lumen, wherein the guide wire lumen defines a continuously sealed fluid path between the proximal end of the shaft and the laterally-facing holes such that fluid injected into the guide wire lumen exits distally of the balloon through the laterally-facing holes.

2. A dilation catheter as in claim 1, wherein the holes are radially spaced.

3. A dilation catheter as in claim 1, wherein the holes are longitudinally spaced.

4. A dilation catheter as in claim 1, wherein the holes are radially and longitudinally spaced.

5. A dilation catheter as in claim 1, wherein the tip is formed integrally with the distal end of the elongate shaft.

6. A dilation catheter as in claim 1, wherein the tip is formed integrally with the distal end of the balloon.

7. A dilation catheter as in claim 1, wherein the inside diameter of the guide wire lumen is greater than 0.040 inches.

8. A dilation catheter as in claim 7, wherein the diameter of the aperture is less than 0.038 inches.

9. A balloon dilation catheter system, comprising:
   (i) a guide wire; and
   (ii) a balloon dilation catheter removably disposed about the guide wire, the balloon catheter comprising:

(a) an elongate shaft having a proximal end and a distal end, the elongate shaft defining a guide wire lumen and an inflation lumen extending therethrough;

(b) an inflatable balloon connected to the distal end of the elongate shaft, the inflatable balloon having a proximal end, a distal end and an interior in fluid communication with the inflation lumen, the guide wire lumen extending through the balloon; and (c) a tip connected to the distal end of the inflatable balloon, the tip defining a distally-facing radially compliant guide wire aperture and a plurality of laterally-facing holes, both the distally-facing radially compliant guide wire aperture and the laterally-facing holes being in fluid communication with the guide wire lumen, wherein the guide wire lumen defines a continuously sealed fluid path between the proximal end of the shaft and the laterally-facing holes such that fluid injected into the guide wire lumen exits distally of the balloon through the laterally-facing holes.

10. A dilation catheter as in claim 9, where in the holes are radially spaced.

11. A dilation catheter as in claim 9, wherein the holes are longitudinally spaced.

12. A dilation catheter as in claim 9, wherein the holes are radially and longitudinally spaced.

13. A dilation catheter as in claim 12, wherein the holes measure about 0.010 inches to about 0.020 inches in diameter and total about 4 to 10 in quantity.

14. A balloon dilation catheter system comprising:

(i) a guide wire having an outside diameter; and (ii) a balloon dilation catheter removably disposed about the guide wire, the balloon catheter comprising:

(a) an elongate shaft having a proximal end and a distal end, the elongate shaft defining a guide wire lumen and an inflation lumen extending therethrough;

(b) an inflatable balloon connected to the distal end of the elongate shaft, the inflatable balloon having a proximal end, a distal end and an interior in fluid communication with the inflation lumen, the guide wire lumen extending through the balloon; and (c) a tip connected to the distal end of the inflatable balloon, the tip defining a distally-facing radially compliant guide wire aperture and a plurality of laterally-facing holes, the distally-facing radially compliant guide wire aperture having a relaxed diameter less than the outside diameter of the removable guide wire, both the distally-facing radially compliant guide wire aperture and the laterally-facing holes being in fluid communication with the guide wire lumen, wherein the guide wire lumen defines a continuously sealed fluid path between the proximal end of the shaft and the laterally-facing holes such that fluid injected into the guide wire lumen exits distally of the balloon through the laterally-facing holes.

15. A dilation catheter system as in claim 14, wherein the tip of the dilation catheter is cup-shaped.

16. A dilation catheter system as in claim 14, wherein the tip of the dilation catheter is conically-shaped.

17. A dilation catheter system as in claim 14, wherein the tip of the dilation catheter includes a plurality of longitudinal slits extending through the tip.

18. A dilation catheter system as in claim 14, wherein the tip of the dilation catheter includes a plurality of longitudinal recesses extending through the tip.

* * * * *